United States Patent [19]

Feld

[11] Patent Number: 4,488,999
[45] Date of Patent: Dec. 18, 1984

[54] METHOD FOR THE RECOVERY OF COBALT OXALATE AND/OR MANGANESE OXALATE

[75] Inventor: Marcel Feld, Cologne, Fed. Rep. of Germany

[73] Assignee: Dynamit Nobel AG, Troisdorf, Fed. Rep. of Germany

[21] Appl. No.: 462,861

[22] Filed: Feb. 1, 1983

[30] Foreign Application Priority Data

Feb. 3, 1982 [DE] Fed. Rep. of Germany ....... 3203658

[51] Int. Cl.$^3$ ............................ C07F 13/00; C07F 5/06
[52] U.S. Cl. ................................. 260/429 R; 562/412; 562/414; 562/493; 260/439 R; 502/24
[58] Field of Search .................. 562/412, 414, 493; 260/429 R, 439 R; 252/413

[56] References Cited

U.S. PATENT DOCUMENTS

| | | |
|---|---|---|
| 3,332,971 | 7/1967 | Elder et al. ..................... 260/439 R |
| 3,803,191 | 4/1974 | Ehrreich et al. ................. 260/439 R |
| 3,840,469 | 10/1974 | Hobbs et al. ................. 260/439 R X |
| 4,170,602 | 10/1979 | Deffeyes et al. ................ 260/439 R |
| 4,314,073 | 2/1982 | Crooks .......................... 562/412 X |
| 4,329,493 | 5/1982 | Hashizume et al. ................ 562/414 |
| 4,346,230 | 8/1982 | Hoffmann et al. ............. 562/412 X |

*Primary Examiner*—Helen M. S. Sneed
*Attorney, Agent, or Firm*—Felfe & Lynch

[57] ABSTRACT

In a process for the recovery of cobalt oxalate and/or manganese oxalate, the solutions or extracts containing cobalt and/or manganese are treated with sodium, potassium or ammonium oxalate. To obtain an easily filtrable cobalt and/or manganese oxalate precipitate, the precipitation is performed at temperatures of 50° to 160° C. with 1 to 2 moles of solid alkali oxalate or ammonium oxalate. When sodium oxalate is used, the water content of the solutions or extracts is from 5 to 90% by weight, when potassium oxalate is used it is from 2 to 15% by weight, and when ammonium oxalate is used it is from 1 to 12% by weight.

4 Claims, No Drawings

METHOD FOR THE RECOVERY OF COBALT OXALATE AND/OR MANGANESE OXALATE

BACKGROUND OF THE INVENTION

The invention concerns a method of recovering cobalt oxalate and/or manganese oxalate from solutions containing cobalt and/or manganese in aqueous acetic acid or in organic solvents or solvent mixtures or extracts which are at least partially miscible with water, by the addition to the solutions or extracts of sodium oxalate, potassium oxalate or ammonium oxalate per mole of dissolved cobalt compound and/or manganese compound.

The method of the invention is particularly suitable for the recovery of cobalt and/or manganese catalysts from acetic acid mother liquors from oxidation processes for the preparation of aromatic carboxylic acids by the oxidation of alkyl aromatics with atmospheric oxygen in acetic acid solution. By oxidation processes such as these, terephthalic acid, for example, is prepared from p-xylene, p-nitrobenzoic acid is prepared from p-nitrotoluene, and other aromatic carboxylic acids are prepared from the corresponding alkyl aromatics.

The recovery of the catalyst is an important factor in the economy of such processes. In most of the methods described for the recovery of catalyst from oxidation mother liquors, such as the one described in DE-OS No. 2,131,470, DE-OS No. 2,260,491 or DE-OS No. 2,419,323, the catalysts are isolated in carbonate form. For this purpose the acetic acid solutions must first be concentrated by evaporation and the residues extracted with water. The extraction of this often tarry, occasionally even two-phase residue, is problematical and not always sufficiently effective. An incomplete extraction of the cobalt, however, signifies not only losses of the relatively expensive catalyst, but it also makes it considerably more difficult to dispose of the residual product still containing cobalt.

A method for the recovery of cobalt and/or manganese catalyst from acetic acid oxidation mother liquors is described in Japanese OS 9,7593/76: the heavy metal catalyst in the oxidation mother liquor is precipitated by the addition of oxalic acid the form of an oxalate of poor solubility, and isolated by solid-from-liquid separation methods. This method offers the possibility of separating other heavy metal oxalates precipitated together with the cobalt and/or manganese oxalate by washing them out.

When the method of Japanese OS 97,593/76 was practiced, it was found that the cobalt oxalate which precipitated from cobalt-containing acetic acid oxidation mother liquors or from acetic acid cobalt acetate solutions is virtually unfiltrable. Even when the precipitation conditions were altered as regards temperature, degree of aqueous dilution of the solution, cobalt concentration or the way in which the oxalic acid was added, ease of filtrability could not be achieved. The addition of filter aids brought no improvement. In all cases, the cobalt and/or manganese oxalate was obtained in a form in which it was virtually unfiltrable with filtration centrifuges or suction or pressure filters.

The reason for the above-described filtration problems in a cobalt oxalate precipitated in accordance with Japanese OS No. 97,593/76 became evident when the product was subjected to examination in the scanning electron microscope: the crystallizate consisted of small, rounded particles of a diameter of only about 0.1 to 0.3 microns. The filtration of such a finely crystalline product is extremely problematical and is impossible using common filtration apparatus such as filtration centrifuges, suction filters or pressure filters under technical conditions, since even in thicknesses of less than 0.5 cm, the fine crystallizate was compressed to a very dense layer that blocked passage of the liquid.

THE INVENTION

It is the object of the invention to recover a cobalt and/or manganese oxalate that is much more coarsely crystalline and easy to filter. This object is achieved by the invention by adding in solid form from 1 to 2 moles of sodium oxalate, potassium oxalate or ammonium oxalate at temperatures of 50° to 160° C. and by making the water content of the solutions or extracts to amount to from 5 to 90% by weight in the case of sodium oxalate, from 2 to 15% by weight in the case of potassium oxalate, and from 1 to 12% by weight in the case of ammonium oxalate.

An essential and surprising requirement of the method of the invention is the establishment of a specific water content in the solutions or extracts involved, according to the kind of oxalate that is added.

Only if all of the relatively narrow conditions characteristic of the invention are fulfilled will the cobalt and/or manganese oxalate be obtained in a fast-settling, easily filtrable form. Examination with the scanning electron microscope of the cobalt oxalate precipitated in Example 3 using sodium oxalate under the conditions of the invention revealed, after an ultrasound treatment to break up agglomerations, acicular crystals most of which had a length of 2 to 5 microns. Prior to the ultrasound treatment, i.e., in the freshly precipitated state, these acicular crystals were still clustered in considerably larger and evidently relatively strong agglomerations, some of them remaining unaffected even after the ultrasound treatment.

In the case of the cobalt oxalate precipitated in Example 8 with the use of ammonium oxalate, the examination of individual crystals and crystals which had grown together into larger particles revealed a principal size of 6 to 16 microns.

The scanning electron microscope studies therefore confirm that, under the conditions in accordance with the invention, the cobalt oxalate is obtained in a decidedly different form which greatly facilitates filtration. The aim of recovering cobalt oxalate and/or manganese oxalate in a more coarsely crystalline, easily filtrable form was thus achieved.

The amount of ammonium or alkali oxalate necessary for a virtually quantitative precipitation of the dissolved cobalt and/or manganese depends on the concentration of the heavy metals. As Example 6 shows, an equivalent amount of oxalate, with respect to the heavy metal concentration, may suffice for the virtually complete precipitation of the cobalt. In most of the examples given, an excess of alkali or ammonium oxalate was used, amounting to approximately 20% with respect to the stoichiometric ratios.

The interaction between solid alkali or ammonium oxalate and the solution of the cobalt and/or manganese salts takes place at elevated temperature, preferably under refluxing conditions. Thus, in Prior-Art Example 9, 60 hours of the action of ammonium oxalate on an acetic acid solution of cobalt acetate at room temperature resulted in a virtually quantitative precipitation of the cobalt, but the cobalt oxalate obtained was scarcely filtrable.

According to the invention, the recovery process is practiced in a temperature range of 50° to 160° C.

It is very important to have a specific water content in the solution from which cobalt and/or manganese are to be precipitated in oxalate form. When sodium oxalate is used for the precipitation of cobalt oxalate and/or manganese oxalate from an acetic acid solution by the method of the invention, the water content of the solution must be greater than 5% by weight. In the case of a water content of 5 wt.-% or less, quantitative cobalt precipitation was not achieved, even after very long reaction times. For example, a 95 wt-% acetic acid with a cobalt content of 5 wt.-%, still had a cobalt concentration of about 300 ppm (=0.03 wt.-%) after 13 hours of treatment with sodium oxalate under refluxing conditions. The cobalt oxalate precipitated under these conditions proved to be virtually unfiltrable under the usual filtration conditions. In the case of an 88 wt.-% acetic acid with the same cobalt concentration, however, the cobalt content dropped to less than 1 ppm after only 4 or 3 hours, depending on the experimental conditions, and the crystallizate could be filtered quite easily.

With regard to the necessary or possible aqueous dilution of an acetic acid solution containing cobalt, the action of sodium oxalate differs decidedly from that of potassium or ammonium oxalate.

If potassium oxalate is used for the precipitation of cobalt oxalate and/or manganese oxalate, the water content of the acetic acid solution must be greater than 2 and less than 15 percent by weight for the achievement of an easily filtrable crystallizate. Both in the case of a water content of 15 wt.-% and more, and in the case of a water content of 2 wt.-% or less, the crystallizate proved to be difficult to filter. Furthermore, in the case of a water content of 2 wt.-% or less, a longer reaction was necessary for the quantitative precipitation of the heavy metal.

If ammonium oxalate is used for the precipitation of cobalt oxalate and/or manganese oxalate, the heavy metal oxalate is precipitated quantitatively in easily filtrable form within a brief reaction time of 2 hours, even when the water content is only 2% by weight. In the case of a 99 wt.-% acetic acid solution, however, 6 hours of reaction with ammonium oxalate resulted in a crystallizate that was difficult to filter. This was also the case when an 88 wt.-% solution of acetic acid was used. Consequently, it appears that, when ammonium oxalate is used, the water content of the solution must be more than 1% and less than 12% by weight.

The demonstrated relationship between the necessary water content of the solution and the kind of oxalate that is used for the precipitation of cobalt and/or manganese makes it possible to adapt the process in an optimum manner to the acetic acid solution that is involved. At the same time, mixtures of sodium, potassium or ammonium oxalate can also be used.

Even though the method of the invention is especially suitable for separating cobalt and/or manganese from acetic acid mother liquors which remain after the separation of the target products in oxidation processes catalyzed by salts of those metals in acetic acid solution, such as for example the oxidation of p-xylene, p-nitrotoluene and other alkyl aromatics, it is by no means limited thereto. It can also be applied to solutions and extracts containing cobalt and/or manganese and originating from other processes, such as carbonylation processes or oxidations in media containing no acetic acid. Neither is it limited to acetic acid as the solvent, but is applicable to other organic solvents such as, for example, alcohols, ethers, ketones and solvent mixtures of different composition.

It is an important requirement for the application of the invention to the separation of cobalt and/or manganese from organic solutions other than acetic acid solutions, that the latter permit the necessary aqueous dilution.

In addition to the isolation of cobalt and/or manganese from acetic acid oxidation mother liquors, the recovery of the metals from processes for the preparation of dimethyl terephthalate by air oxidation of p-xylene and p-toluylic acid methyl ester mixtures represents a possibility for the application of the method of the invention that is important from the economical point of view. In this multiple step process for the production of dimethyl terephthalate, cobalt and manganese salts are used as catalysts in the oxidation, which is performed in a medium which does not contain acetic acid. Afterward, the heavy metals are found in distillation residues from which they can be extracted with appropriate solvents, such as acetic acid, acetone or methyl glycol, for example. In that case, however, organic byproducts get into the extract and might interfere with the oxidation. The method of the invention offers a possibility for the precipitation of the heavy metal oxalates which can then be separated from the organic byproducts.

In the examples described hereinbelow, the filtration was always performed as a vacuum filtration, using always the same apparatus. The filters had a diameter of 27 mm and a filtration time of 6 to 12 sec as determined in accordance with DIN 53,137. The filtration times given include the washing. The testing of the mother liquids for the residual content of cobalt(II) ions was performed with test sticks for $Co^{2+}$. The tests were made after not less than 2 hours of reaction time. Where the reaction time was longer than 2 hours this resulted from the requirement of a virtually quantitative precipitation of the cobalt, which was considered to be achieved when the residual content in the mother liquor was less than 1 ppm.

EXAMPLES

Examples 1 to 10 of the Invention

Crystalline sodium, potassium or ammonium oxalate was added to a solution of 2.1 g of cobalt acetate tetrahydrate in 100 g of acetic acid, and the mixture was refluxed, with stirring. The suspension was cooled to room temperature and filtered and the filter cake washed with 10 g of acetic acid. The kind and amount of the oxalate, the concentration of the acetic acid in the dilute aqueous acetic acid solution, the reaction time and the filtration time are given in Table 1.

TABLE 1

| | EXAMPLES OF THE INVENTION | | | | | |
|---|---|---|---|---|---|---|
| Example No. | sodium oxalate (g) | potassium oxalate (g) | ammonium oxalate (g) | acetic acid (wt %) | reaction time (h) | filtration time (min) |
| 1 | 1.5 | | | 10 | 2 | 3 |
| 2 | 1.5 | | | 88 | 4 | 6 |
| 3* | 1.5 | | | 88 | 3 | 4 |
| 4 | 1.5 | | | 90 | 7 | 6 |
| 5 | | 1.7 | | 90 | 2 | 8 |
| 6 | | 1.55 | | 95 | 2 | 4 |

TABLE 1-continued

| | EXAMPLES OF THE INVENTION | | | | | |
|---|---|---|---|---|---|---|
| Example No. | sodium oxalate (g) | potassium oxalate (g) | ammonium oxalate (g) | acetic acid (wt %) | reaction time (h) | filtration time (min) |
| 7 | | 4.6 | | 95 | 2 | 6 |
| 8 | | | 1.5 | 93 | 2 | 6 |
| 9 | | | 1.5 | 95 | 2 | 2 |
| 10 | | | 1.5 | 98 | 2 | 2 |

*Oxalate added to the warm solution.

Prior-Art Examples 1 to 8

The Prior-Art Examples 1 to 9 were performed similarly to Examples 1 to 10 of the invention at different aqueous acetic acid concentrations (dilutions) as listed in Table 2.

TABLE 2

| | PRIOR-ART EXAMPLES | | | | | |
|---|---|---|---|---|---|---|
| Example No. | sodium oxalate (g) | potassium oxalate (g) | ammonium oxalate (g) | acetic acid (wt %) | reaction time (h) | filtration time (min) |
| 1* | 1.5 | | | 95 | 13 | n. f. |
| 2 | | 1.7 | | 80 | 2 | 40 |
| 3 | | 1.7 | | 85 | 2 | 25 |
| 4 | | 1.7 | | 98 | 3 | 25 |
| 5 | | 1.7 | | 99 | 5 | 45 |
| 6 | | | 1.5 | 80 | 2 | n. f. |
| 7 | | | 1.5 | 88 | 2 | 60 |
| 8 | | | 1.5 | 99 | 6 | 35 | n. f.: Not filtrable under the usual conditions.
*Solution still contained 300 ppm of $Co^{2+}$

Prior-Art Example 9

Prior-Art Example 9 was performed similarly to Example 9 of the invention as regards the concentrations, but the ammonium oxalate was added at room temperature and thereafter was not heated. A quantitative precipitation of the cobalt was achieved after 60 hours, and the filtration time was 45 minutes.

Prior-Art Example 10

1.5 g of ammonium oxalate, dissolved in 5 g of water, was added to 2.1 g of cobalt acetate tetrahydrate, dissolved in 95 g of acetic acid, and the suspension thus formed was refluxed for 4 hours. Upon cooling to room temperature no settling took place. Under the specified filtration conditions the suspension proved to be unfiltrable. The filtrate initially obtained was very turbid and the rate of filtration diminished rapidly until at least the passage of the liquid was completely blocked by the filter for more than half of the total suspension.

Prior-Art Example 11

2.1 of cobalt acetate tetrahydrate, dissolved in 100 g of a 93 wt.-% acetic acid solution, was treated at room temperature with 1.3 g of oxalic acid, with stirring, and then stirred for one hour at room temperature. The suspension was not filtrable under the stated filtration conditions. The product consisted of rounded primary particles of a diameter of 0.1 to 0.3 microns.

Example 11 of the Invention 2.1 g of manganese acetate tetrahydrate was dissolved in 100 g of 95 wt.-% of heated acetic acid; then 1.5 g of ammonium oxalate was added and the mixture was refluxed, with stirring, for 2 hours. The suspension, cooled to room temperature, was filtered and the filter cake was washed with 10 g of acetic acid. The filtration time was 8 minutes, and the manganese content remaining in the mother liquor was less than 2 ppm.

Example 12 of the Invention 113.6 g of mother liquor remaining from the oxidation of p-nitrotoluene with atmospheric oxygen in acetic acid solution and having a cobalt content of 0.55 wt.-% and a water content of 62 wt.-%, was treated, after removal of the p-nitrobenzoic acid target product by filtration, with 2.0 g of ammonium oxalate and then refluxed for 2 hours with stirring. After the mixture had cooled to room temperature it was filtered and the filter cake was washed with 10 g of acetic acid. The filtration time was 3 minutes, and the mother liquor had a cobalt content of less than 1 ppm.

Example 13 of the Invention 94 g of a solution of cobalt naphthenate in isopropanol, with a cobalt content of 0.5 wt.-%, was first treated with 12 g of water and then with 2.3 g of ammonium oxalate monohydrate and refluxed for 3 hours with stirring. The suspension was cooled to room temperature and filtered under the usual conditions for a period of 15 minutes. The cobalt content of the mother liquor was then found to be less than 1 ppm.

It will be understood that the specification and examples are illustrative but not limitative of the present invention and that other embodiments within the spirit and scope of the invention will suggest themselves to those skilled in the art.

What is claimed is:

1. A process for recovering cobalt and/or manganese as the oxalates from solution, in acetic acid, organic solvent or solvent mixtures or extracts, which is at least partially miscible with water, comprising mixing the solution of extract with 1 or 2 moles in solid form of sodium, potassium or ammonium oxalate while maintaining the mixture at a temperature in the range of from about 50° C. to about 160° C. and at a water content of 5 to 90 weight-percent if sodium oxalate is used, 2 to 15 weight-percent if potassium oxalate is used, or 1 to 12 weight-percent if ammonium oxalate is used, thereby to form an easily filterable suspension of cobalt and/or manganese oxalate.

2. The process of claim 1 further comprising separating the cobalt and/or manganese oxalate suspension from the reaction mixture.

3. The process of claim 1 further comprising filtering the reaction mixture to remove the cobalt and/or manganese oxalate.

4. The process of claim 1 wherein the solution of cobalt and/or manganese to be treated is a mother liquor or reaction solution from processes for the preparation of aromatic carboxylic acids by oxidation of alkyl aromatics in the presence of an aliphatic monocarboxylic acid as solvent and of cobalt and/or manganese catalyst.

* * * * *